United States Patent [19]

Magyar et al.

[11] Patent Number: 4,871,722

[45] Date of Patent: Oct. 3, 1989

[54] SYNERGISTIC VETERINARY COMPOSITION AND/OR FODDER PREMIX AND PROCESS FOR PREPARING SAME

[75] Inventors: Károly Magyar; János Varga; Ferenc Simon; Hedvig Szauder née Laukó; Pál Fekete; Attila Romváry; János Egri; Katalin Zukovics náe Someg, all of Budapest, Hungary

[73] Assignee: EGIS Gyogyszergvar, Budapest, Hungary

[21] Appl. No.: 158,757

[22] Filed: Feb. 22, 1988

[30] Foreign Application Priority Data

Feb. 25, 1987 [HU] Hungary ................................ 719/87

[51] Int. Cl.$^4$ ............................................ A61K 31/635
[52] U.S. Cl. .................................... 514/157; 514/275; 514/311
[58] Field of Search ........................ 514/157, 275, 311

[56] References Cited

U.S. PATENT DOCUMENTS 3,382,148  5/1968  Thommen ............................ 514/275

FOREIGN PATENT DOCUMENTS 0043055  6/1981  European Pat. Off. ............ 514/157
7316608  12/1970  Japan .................................... 514/157
2030863  4/1980  United Kingdom ................ 514/157

*Primary Examiner*—Frederick E. Waddell
*Attorney, Agent, or Firm*—Keil & Weinkauf

[57] ABSTRACT

The invention relates to a synergistic veterinary composition and/or a fodder premix useful for preventing or curing bacterial, fungal and protozoic infection particularly occurring at poultry species. Furthermore the invention relates to a process for preparing same. The composition or premix contains 1 to 100 parts by mass of 2,4-diamino-5-(3,4,5-trimethoxybenzyl)pyrimidine and/or 1 to 100 parts by mass of 2,4-diamino-5-(3,4-dimethoxybenzyl)pyrimidine as well as 1 to 100 parts by mass of 2,6-dimethoxy-4-sulfanilamidopyrimidine or a pharmaceutically acceptable salt thereof and 1 to 100 parts by mass of 8-hydroxyquinoline or a pharmaceutically acceptable acid addition salt thereof optionally in admixture with carrier(s) and/or additive(s) commonly used in the pharmaceutical industry or for the preparation of premixes.

5 Claims, No Drawings

SYNERGISTIC VETERINARY COMPOSITION AND/OR FODDER PREMIX AND PROCESS FOR PREPARING SAME

The invention relates to a synergistic veterinary composition and/or a fodder premix useful to prevent or cure bacterial, fungal, and protozoic (hereafter: bacterial) infections particularly occurring at poultry species.

According to an other aspect of the invention, there is provided a process for the preparation of these compositions and premixes.

The death of animals in the poultry-farming is caused by various bacterial infections such as chicken cholera, pneumomycosis, coccidiosis and the like. In addition to these veterinary diseases the death of chicklings, highly influencing the economy of poultry-farming, is mainly due to *Escherichia coli, Salmonella typhimurium* and eventually *Staphylococcus aureus* infections.

Various drugs are used for combatting the above infections.

According to the Hungarian patent specification No. 181,027 the combination of 2,4-diamino-5-(3,4,5-trimethoxybenzyl)pyrimidine (trimetoprim) with N-(2-chinoxalinyl)sulfanilamide (sulfachinoxaline) is useful for combatting bacterial and protozoic poultry diseases. A drawback of this known composition consists in that, owing to the toxicity of sulfachinoxaline, the haemopoietic organs and vessel walls of the animals are significantly injured. In addition, though this composition is relatively active against coccidiosis, it should be used in relatively high doses against the most frequent bacterium strains.

In case of more widespread infections, the animals are treated with antibiotics to diminish the deaths. The disadvantage of using antibiotics consists in the resistance appearing after a relatively short treatment period. Further on, resistance may also appear in the people consuming the meat of poultry treated with antibiotics.

Thus, there exists a demand on veterinary compositions effectively inhibiting the problematic infections occurring in the poultry-farming. In this aspect, the treatment of chicken cholera induced by Pasteurella multocida bears a high economic importance.

We have investigated the possibility of treating the above infections with the antibacterial compositions used in veterinary therapeutics. From the sulfonamides, 2,6-dimethoxy-4-sulfanilaminopyrimidine (sulfadimethoxine) is one of the least toxic ones inducing, in contrast to sulfaquinoxaline, no damages of the haemopoietic organs and vessel walls. Based on the British patent specification No. 875,562 the antibacterial effect of sulfonamides can be potentiated by trimetoprim. According to our investigations, as it is shown in Table 1, the in vitro bacterial growth is not better inhibited by an 1:1 mixture of trimetoprim with sulfadimethoxine than by the individual components.

Now it has been found that the combination of 2,4-diamino-5-(3,4,5-trimethoxybenzyl)pyrimidine (trimetoprim) and/or 2,4-diamino-5-(3,4-dimethoxybenzyl)pyrimidine (diaveridine) with 2,6-dimethoxy-4-sulfanilamidopyrimidine (sulfadimethoxine) and 8-hydroxyquinoline exerts a strong antibacterial effect on bacterium strains most frequently infecting the poultry.

Although each of the above compounds has an own in vitro antibacterial effect, a very high dose of either trimetoprim or diaveridine or sulfadimethoxine is necessary for the inhibiting effect. In vitro a relatively low dose of 8-hydroxyquinoline is active, in vivo, however, the required therapeutic blood level cannot develop in the blood plasma. Thus, it is surprising for a person skilled in the art that 0.1 µg/ml of trimetoprim or diaveridine, respectively, together with 0.1 µg/ml of sulfadimethoxine and 0.1 µg/ml of 8-hydroxyquinoline sulfate exert an in vitro bactericidal effect on e.g. the Pasteurella multocida strain.

This observation is supported by the experimental results discussed hereinafter.

The minimum inhibiting concentration (MIC) values of the above compounds and their two- or three-component combinations were determined in phenol-red - glucose broth (product of the Difco Co.) by using the broth-dilution method on the following bacterium strains isolated from chickens:

A: *Staphylococcus aureus*
B: *Escherichia coli* 1
C: *Escherichia coli* 2
D: *Salmonella typhimurium*
E: *Pasteurella multocida*
F: *Aspergillus fumigatus*

The MIC values (in µg/ml providing the bactericidal effect are shown in Table 1.

TABLE 1

| Test compound | MIC value (µg/ml) for the bacterium strain | | | | | |
|---|---|---|---|---|---|---|
| | A | B | C | D | E | F |
| Trimetoprim | 200 | 200 | 200 | 200 | 100 | 200 |
| Diaveridine | 200 | 200 | 150 | 200 | 150 | 200 |
| Sulfadimethoxine | 200 | 200 | 200 | 200 | 200 | 200 |
| 8-Hydroxyquinoline sulfate | 5 | 25 | 25 | 50 | 1 | 25 |
| 1:1 by mass mixture of trimetoprim with sulfadimethoxine | 200 | 200 | 200 | 200 | 200 | 100 |
| 1:1 by mass mixture of diaveridine with sulfadimethoxine | 200 | 200 | 200 | 200 | 200 | 200 |
| 1:1 by mass mixture of trimetoprim with 8-hydroxyquinoline sulfate | 10 | 50 | 50 | 50 | 1 | 50 |
| 1:1 by mass mixture of diaveridine with 8-hydroxyquinoline sulfate | 10 | 50 | 50 | 50 | 2 | 50 |
| 1:1:1 by mass mixture of trimetoprim with sulfadimethoxine and 8-hydroxyquinoline sulfate | 3 | 10 | 10 | 15 | 0.3 | 10 |
| 1:1:1 by mass mixture of diaveridine with sulfadimethoxine and 8-hydroxyquinoline sulfate | 4 | 15 | 15 | 10 | 0.3 | 10 |

It is evident from Table 1 that in case of the bacterium strains tested, in the combination of the invention trimetoprim, diaveridine and sulfadimethoxine are in vitro active in the 1/40th to 1/1000th part and 8-hydroxyquinoline sulfate in the 1/5th to 1/10th part of their separately determined MIC value.

According to the invention, usually 1 to 100 parts by mass of trimetoprim and/or 1 to 100 parts by mass of diaveridine as well as 1 to 100 parts by mass of sulfadimethoxine and 1 to 100 parts by mass of 8-hydroxyquinoline are mixed optionally together with carrier(s) and additive(s) commonly used in the pharmaceutical industry and/or in the preparation of premixes.

The active ingredients may also be used in the form of their therapeutically acceptable salts or acid addition salts. Sulfadimethoxine is preferably used as sodium salt and 8-hydroxyquinoline as sulfate.

It is particularly preferable to mix the active ingredients or their pharmaceutically acceptable salts in the same mass ratio.

The mixture of sulfadimethoxine and 8-hydroxyquinoline with trimetoprim and/or diaveridine may orally be administered to the animals as such, e.g. as dissolved in drinking-water or mixed to the fodder; or, it may be formulated to a veterinary composition by using the carriers commonly used in the pharmaceutical industry.

According to a preferred embodiment of the process of the invention, pharmaceutical compositions, preferably water-soluble or suspendable powder mixtures or suspensions, are prepared. Sugars or starch hydrolysates are suitably used as pharmaceutically acceptable carriers. The pharmaceutical compositions may also contain various additives, e.g. vitamins, mineral salts, trace elements, antioxidants, suspending, emulsifying and dispersing agents and the like.

A preferred powder mixture contains 15 parts by mass of a mixture of the active ingredients together with 35 parts by mass of a pharmaceutically acceptable carrier. This composition is dissolved or suspended in 100,000 parts by mass of drinking-water for treating the animals.

According to another preferred embodiment of the process of the invention, the mixture of the active ingredients or the powder-like pharmaceutical composition prepared therefrom is added to the fodder. For assuring uniform mixing-in, first a fodder premix is suitably prepared which is then mixed to the fodder.

According to a preferred method of preparing the powder premix, the active ingredients are mixed with carrier(s) and/or additive(s) commonly used for preparing premixes. Suitable carriers are e.g. wheat meal (fodder meal), wheat bran, corn meal, rice bran free from oil, soy meal, starch, silicon dioxide, kaolin, zeolite, calcium carbonate and the like. Preferred carriers are silicon dioxide and starch, e.g. corn starch or potato starch. Trace elements, vitamins, inorganic salts and the like may be used as additives.

Usually, the fodder premix contains the active ingredients in an amount of 1 to 50% by mass; mostly, 0.001 to 1% by mass of premix is mixed to the food of the poultry.

Trimetoprim, diaveridine, sulfadimethoxine and 8-hydroxyquinoline all are known and commercially available substances.

The treatment by using a veterinary composition of the invention, or the feeding of the animals with the premix of the invention as mixed to the powder may be performed as a therapeutic intervention at the appearance of symptoms of the acute infection or as a preventive treatment starting from the babychick age.

By using the composition or the premix of the invention, an effective combatting of several bacterial infections of the poultry is possible. The strong inhibitory effect exerted on the Pasteurella multacida strain (inducing the chicken cholera) bears a particular economic importance since there exists no successful specific therapy for this disease.

The invention is illustrated in detail by the following non-limiting Examples.

EXAMPLE 1

15 kg of trimetoprim are mixed with 15 kg of sulfadimethoxine, 15 kg of 8-hydroxyquinoline sulfate and 450 kg or corn starch. One part by mass of the premix thus obtained is mixed into 100 parts by mass of poultry food, and the animals are fed with the thus-obtained food.

EXAMPLE 2

One kg of diaveridine is mixed with 1 kg of sulfadimethoxine, 1 kg of 8-hydroxyquinoline sulfate and 60 kg of silicon dioxide. One part by mass of the premix thus obtained is mixed into 100 parts by mass of poultry food before use.

EXAMPLE 3

4.5 g of trimetoprim, 4.5 g of sulfadimethoxine sodium salt and 7.5 g of 8-hydroxyquinoline sulfate are mixed with 30 g of polyvinylpyrrolidone and 20 g of citric acid. The thus-obtained powder mixture is dissolved in 2 liters of tap water and then diluted to 100 litres with the drinking-water of the poultry.

EXAMPLE 4

4.5 g of trimetoprim, 4.5 g of sulfadimethoxine sodium salt and 4.5 g of 8-hydroxyquinoline sulfate are mixed with 20 g of polyvinylpyrrolidone and 20 g of tartaric acid. the thus-obtained powder mixture is dissolved in 2 liters of tap water then diluted to 100 litres with the drinking-water of the poultry.

We claim:

1. A synergistic veterinary composition and/or fodder premix for the prevention or curing of bacterial infections occurring in poultry, which comprises 1 to 100 parts by mass of 2,4-diamino-5-(3,4,5-trimethoxybenzyl)pyrimidine and/or 1 to 100 parts by mass of 2,4-diamino-5-(3,4-dimethoxybenzyl) pyrimidine as well as 1 to 100 parts by mass of 2,6-dimethoxy-4-sulfanilamidopyrimidine or a pharmaceutically acceptable salt thereof and 1 to 100 parts by mass of 8-hydroxyquinoline or a pharmaceutically acceptable acid addition salt thereof optionally in admixture with carrier(s) and/or additive(s) commonly used in the pharmaceutical industry or for the preparation of premixes.

2. A composition and/or fodder premix as claimed in claim 1, wherein the active ingredients are in the same mass ratio.

3. A method for preventing or curing bacterial infections occurring in poultry which comprises treating the bacterially infected or likely to be infected poultry and/or their fodder or water with a bactericidally effective amount of a composition which comprises 1 to 100 parts by mass of 2,4-diamino-5-(3,4,5-trimethoxybenzyl)-pyrimidine and/or 1 to 100 parts by mass of 2,4-diamino-5-(3,4-dimethoxybenzyl) pyrimidine as well as 1 to 100 parts by mass of 2,6-dimethoxy-4-sulfanilamidopyrimidine or a pharmaceutically acceptable salt thereof and 1 to 100 parts by mass of 8-hydroxyquinoline or a pharmaceutically acceptable acid addition salt thereof optionally with carrier(s) and/or additive(s) commonly used in the pharmaceutical industry or for the preparation of fodder premixes.

4. A method as defined in claim 1, wherein the composition contains the active ingredients in the same mass ratio.

5. A method as defined in claim 1, wherein the poultry and/or their fodder or water are treated to prevent or cure bacterial infection from *Staphylococcus aureus, Escherichia coli* 1, *Escherichia coli* 2, *Salmonella typhimurium, Pasteurella multocida* and/or Aspergillus fumigatus.

* * * * *